(12) United States Patent
Cho et al.

(10) Patent No.: US 7,937,137 B2
(45) Date of Patent: May 3, 2011

(54) METHODS OF IDENTIFYING AND/OR ASSESSING CARDIAC ARRHYTHMIAS USING AN IMPLANTABLE MEDICAL DEVICE

(75) Inventors: Yong K. Cho, Maple Grove, MN (US); Tommy D. Bennett, Shoreview, MN (US); Barbro M. Kjellstrom, Minneapolis, MN (US); Susan C. Vadneis, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1454 days.

(21) Appl. No.: 11/342,397

(22) Filed: Jan. 30, 2006

(65) Prior Publication Data
US 2007/0179383 A1 Aug. 2, 2007

(51) Int. Cl.
*A61B 5/0452* (2006.01)
(52) U.S. Cl. .......................................... 600/515
(58) Field of Classification Search .................... 600/515
See application file for complete search history.

(56) References Cited

U.S. PATENT DOCUMENTS

| | | | |
|---|---|---|---|
| 5,184,614 A | 2/1993 | Collins et al. | |
| 5,193,535 A | 3/1993 | Bardy et al. | |
| 5,314,430 A | 5/1994 | Bardy | |
| 5,330,505 A | 7/1994 | Cohen | |
| 5,331,966 A | 7/1994 | Bennett et al. | |
| 5,353,752 A | 10/1994 | Suzuki | |
| 5,353,800 A | 10/1994 | Pohndorf et al. | |
| 5,368,040 A | 11/1994 | Carney | |
| 5,379,776 A | 1/1995 | Murphy et al. | |
| 5,535,752 A | 7/1996 | Halperin et al. | |
| 5,564,434 A | 10/1996 | Halperin et al. | |
| 5,615,684 A | 4/1997 | Hagel et al. | |
| 5,941,831 A | 8/1999 | Turcott | |
| 6,024,704 A | 2/2000 | Meador et al. | |
| 6,152,885 A | 11/2000 | Taepke | |
| 6,731,978 B2 | 5/2004 | Olson et al. | |
| 6,748,269 B2 * | 6/2004 | Thompson et al. | 607/4 |
| 6,865,419 B2 | 3/2005 | Mulligan et al. | |
| 7,174,209 B2 * | 2/2007 | Thompson et al. | 607/9 |
| 2001/0034488 A1 | 10/2001 | Policker et al. | |
| 2004/0092836 A1 | 5/2004 | Ritscher et al. | |
| 2007/0156057 A1 * | 7/2007 | Cho et al. | 600/513 |
| 2007/0255331 A1 * | 11/2007 | Gillberg et al. | 607/36 |
| 2008/0269627 A1 * | 10/2008 | Cho et al. | 600/521 |

FOREIGN PATENT DOCUMENTS
WO  WO 01/70103  9/2001

* cited by examiner

*Primary Examiner* — Eric D. Bertram
(74) *Attorney, Agent, or Firm* — Stephen W. Bauer; Reed A. Duthler (57) ABSTRACT

Apparatus using one or more modes of statistical analysis with one or more monitored parameters of a patient's heart to identify and/or assess arrhythmias. Through use of the one or more modes of statistical analysis, a medical professional can be aided during evaluation of patient data for diagnosis of the patient. At least one of the monitored parameters may include one or more values used representatively for storage intervals of a selected length. As such, for each storage interval, a value may be determined for the one monitored parameter occurring at an upper percentile and a lower percentile. In addition, a median value may be determined for the one monitored parameter for each storage interval. Over a plurality of the storage intervals, these determined values can be used in one or more modes of statistical analysis to better identify and assess the arrhythmias.

6 Claims, 9 Drawing Sheets

METHODS OF IDENTIFYING AND/OR ASSESSING CARDIAC ARRHYTHMIAS USING AN IMPLANTABLE MEDICAL DEVICE

BACKGROUND

The present invention relates to medical devices, and, more particularly, to implantable medical devices.

Typically, patients with heart failure have a reduced capacity for myocardial function. The heart is unable to adequately meet the metabolic demands of the body by providing the appropriate blood flow. This may result in increased blood pressure (afterload), and increased volume retention (preload). Thus, common symptoms of heart failure or ventricular dysfunction include fatigue, which is caused by the low cardiac output, and edema and swelling, which is caused by fluid overload.

In patients with heart failure, on-going ambulatory monitoring of the heart conditions can be an important factor in successful cardiac disease management. Such ambulatory monitoring of the patient can often involve the collection of parameters such as heart rate, pressure, temperature, etc. As is known, the monitoring of one or more of these parameters can be achieved through the use of one or more implantable medical devices (IMDs), such as pacemakers, defibrillators, monitors, etc. Following transfer of these parameters from the IMD(s) to a clinical center, a medical professional, after subsequent analysis, can generally provide final diagnoses concerning the patient.

However, quite often, the collection of these parameters can be limited by the location of the IMD electrode and/or the fixed storage memory size of the IMD. In turn, it can be difficult for the medical professional to identify arrhythmias based on these parameters because of the above limiting factors or other factors. As such, it can also be difficult for the medical professional to routinely provide accurate diagnoses for the patient because of uncertainty regarding whether the parameters are representative of a worsening state of the patient's heart, or conversely, due to an arrhythmic event.

Certain embodiments of the invention are directed to overcoming, or at least reducing the effects of, one or more of the limitations set forth above.

SUMMARY OF THE INVENTION

Embodiments of the invention involve using one or more monitored parameters of a patient's heart to identify and/or assess arrhythmias. As a result, a medical professional can be aided during evaluation of patient data for diagnosis of the patient. In some of the embodiments, at least one of the monitored parameters includes one or more values used representatively for storage intervals of a selected length. In such embodiments, for each storage interval, a value can be determined for the one monitored parameter occurring at an upper percentile and a lower percentile. In addition, a median value can be determined for the one monitored parameter for each storage interval. Over a plurality of the storage intervals, these determined values can be used in one or more modes of statistical analysis to better identify and assess the arrhythmias.

In some embodiments, the at least one monitored parameter includes heart rate. In such embodiments, a "criteria mode" of statistical analysis can be used to determine when one of the determined values of the at least one monitored parameter exceeds a designated setting. If, previous to this one determined value, the one monitored parameter is also found to have increased by a certain set amount, the "criteria mode" is configured to indicate the presence of an arrhythmic event. In further embodiments, a "ratio mode" of statistical analysis can be used to determine the distances between one or more of the determined values of the at least one monitored parameter. By calculating a ratio of these distances, the "ratio mode" is configured to indicate the presence of an arrhythmic event and/or a duration of the arrhythmic event.

In further embodiments, one of the monitored parameters includes cardiac pressure data. In such embodiments, a "variability mode" of statistical analysis can be used with respect to the pressure data with one or more other monitored parameters to further confirm a perceived arrhythmic event.

DETAILED DESCRIPTION

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

Figure 1:
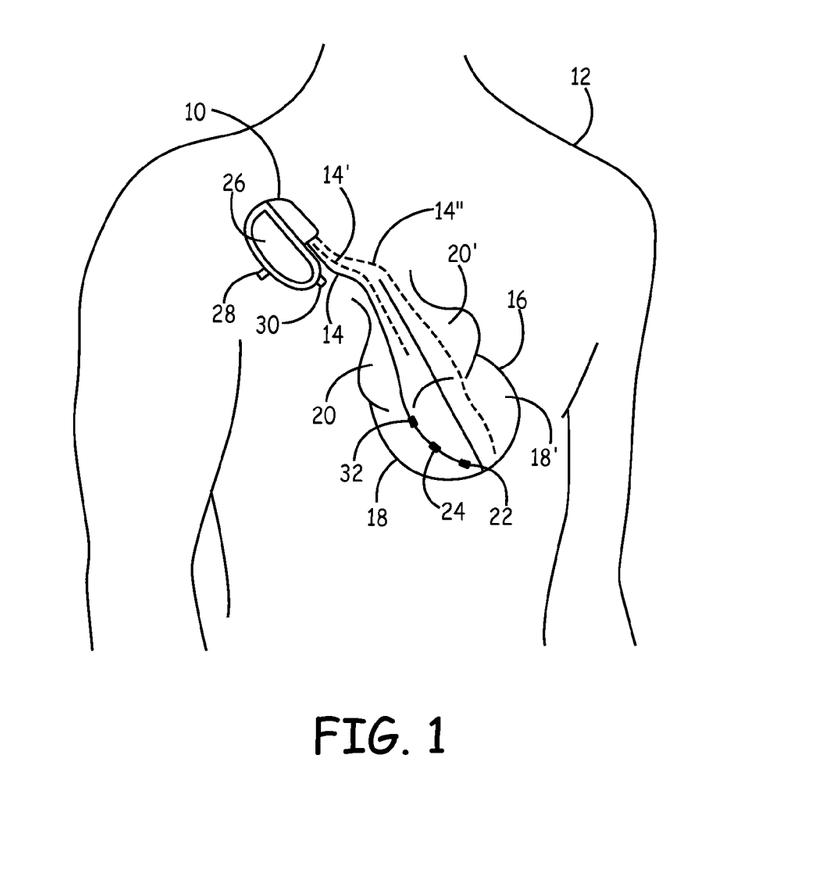
FIG. 1 is a schematic view of a system including an implantable medical device (IMD) in accordance with certain embodiments of the invention.

FIG. 1 is a simplified schematic diagram representation of a system in accordance with certain embodiments of the invention. As shown, an IMD 10 is located in a patient 12. The IMD 10 includes one or more leads extending between the IMD 10 and the heart 16 of the patient 12. For example, as shown, one lead 14 can extend to one of the ventricles, e.g., the right ventricle 18. As such, the IMD 10 can be a single chamber device; however, the invention should not be limited as such. Instead, as mentioned above, it is to be appreciated that the IMD 10 can alternatively, or in combination, include other leads (e.g., leads 14' and/or 14") extending to other distinct areas of the heart (e.g., respectively, to one or more of the atria 20, 20' and/or the left ventricle 18' of the heart 16). As such, the IMD 10 can include any medical device having single or multi-chamber functionality. Alternatively, other devices such as implantable drug delivery devices can also be adapted for use with the current invention.

In certain embodiments, the IMD 10 is an implantable hemodynamic monitor (IHM). However, it is to be appreciated that the invention should not be limited to such a device. Generally, any form of implantable medical device suitable for storing telemetered signals or physiological data could be used, as known in the art. In certain embodiments in which an IHM is utilized, the monitor can include circuitry for data storage and for recovering and processing of cardiac parameters, such as pressure, electrogram, heart rate, core temperature, and activity data. Such an IHM can generally be used in patients with Chronic Heart Failure (CHF), undergoing serial clinical management, and is typically used to complement existing CHF therapies and disease management regimens in order to provide precise therapy management and early intervention by remote monitoring of impending decompensation, so as to improve quality of life. In addition, such an IHM generally contains an operating system that may employ a microcomputer or a digital state machine for timing, sensing, data storage, recovery and processing of pressure, electrogram, heart rate and other related data, to thereby monitor the hemodynamic environment.

An exemplary IHM and its associated leads and circuitry are described in commonly-assigned U.S. Pat. Nos. 5,535,752; 5,564,434; 6,024,704; and 6,152,885, which are incorporated herein by reference in relevant parts. Other pacing systems known in the art may be adapted for use in the alternative. The IMD 10 can additionally, or in the alternative, include cardioversion/defibrillation circuitry as described in commonly-assigned U.S. Pat. Nos. 5,193,535, and 5,314,430, which are incorporated herein by reference in relevant parts. The leads and circuitry disclosed in the above-incorporated, commonly assigned, '752 and '434 patents can be employed to record EGM and absolute blood pressure values over certain time intervals. In certain embodiments, the recorded data can be periodically telemetered from the IMD 10 (e.g., to a programmer) so as to be later evaluated by a physician or other medical professional. In certain embodiments, the data is transmitted from the IMD 10 during a telemetry session. It should be appreciated that such sessions can involve communications with programmers and/or networks (e.g., via web links) so as to enable the provision of the data from the IMD 10 to the physician or medical professional.

With continued reference to FIG. 1, the IMD 10 can be implanted subcutaneously, between the skin and the ribs of the patient 12. Other implantation sites may be used if appropriate. As described above, in certain embodiments, the lead 14 is passed through a vein into the right ventricle 18 of the heart 16. The distal end of the lead 14 or catheter may have a tip electrode 22 contacting the interior of the heart 16. In a multipolar configuration, a second ring electrode 24 may be spaced from the tip electrode 22. Each of these electrodes is connected to the circuitry contained in the IMD 10. Alternatively, a unipolar mode may be used wherein a portion of the metallic enclosure or "can" of the IMD 10 can form an electrode surface 26. As such, the EGM signal is measured between this surface 26 and an implanted electrode, such as the tip electrode 22. In yet another embodiment, a Subcutaneous Electrode Array (SEA) such as electrodes 28 and 30 can be located on, but electrically isolated from, the housing of the IMD 10, such as disclosed in U.S. Pat. No. 5,331,966, incorporated herein by reference in relevant part.

The lead 14 is shown to further include a pressure sensor 32. If desired, an additional lead (not shown) coupled to IMD 10 may be provided to carry the pressure sensor. In certain embodiments, the pressure sensor 32 is located within the right ventricle 18, although it may instead be located within the left ventricle 18'. Pressure sensors and accompanying circuitry that may be adapted for use with embodiments of the invention are described in commonly-assigned U.S. Pat. Nos. 5,353,752, 5,353,800, 5,564,434, 5,330,505, and 5,368,040 which are incorporated herein by reference in their relevant parts.

Generally, an IHM can be used for recording a variety of hemodynamic parameters in a patient with heart failure, for example, including right ventricular (RV) systolic and diastolic pressures (RVSP and RVDP), estimated pulmonary artery diastolic pressure (ePAD), pressure changes with respect to time (dP/dt), heart rate, activity, and temperature. Some parameters can be derived from others, rather than being directly measured. For example, the ePAD parameter can be derived from RV pressures at the moment of pulmonary valve opening, and heart rate can be derived from information in an intracardiac electrogram (EGM) recording. Hemodynamic pressure parameters can be obtained by using a pressure sensor mounted on a lead to measure intracardiac blood pressures, including absolute and/or relative pressures. U.S. Pat. No. 6,865,419 to Mulligan et al., incorporated herein by reference in its relevant part, discloses a method of deriving mean pulmonary arterial pressure (MPAP) from an IHM.

Information collected by the IMD 10 can be retrieved and transmitted to an external device, or to a patient management network, or to a database, using various transmission methods including the Internet. For example, a patient can activate the device to retrieve and transmit the data stored in the IMD 10 to a remote system, where additional processing may be performed on the data. This retrieval and transmission of stored data can be done on a periodic basis, e.g., once per week, to provide a convenient method of "continuous" monitoring of a patient. Stored data retrieved from the IMD 10 and transmitted to a remote system can be available for transfer to a clinical center for review by a medical professional. In certain embodiments, data is transferable to an internet-compatible central patient management network for remote monitoring. A bi-directional communication system that is network, Internet, intranet and worldwide web compatible to enable chronic monitoring based on data obtained from implantable monitors is generally disclosed in International Publication No. WO 01/70103 A2, to Webb et al, incorporated herein by reference in its relevant part.

As described above, the data stored by the IMD 10 can include various parameters that are continuously monitored, for example, the IMD 10 may record intracardiac EGM data at sampling rates as fast as 256 Hz or faster. In certain embodiments, the IMD 10 can alternately store summary forms of data that allows for storage of data representing longer periods of time. For example, in certain embodiments, if the IMD 10 is an IHM, hemodynamic pressure parameters can be summarized by storing a number of representative values that describe the hemodynamic parameter over a given storage interval. The mean, median, an upper percentile, and a lower percentile are examples of representative values that can be stored by the IMD 10 to summarize data over an interval of time (e.g., the storage interval). In this manner, the memory of the IMD 10 can be used to provide hourly, weekly or monthly (or longer) views of the data stored depending on the length of the storage interval selected. The data buffer of the IMD 10, for example, may acquire data sampled at a 256 Hz sampling rate over the certain storage intervals, and the data buffer can be cleared out after the selected representative values during that corresponding storage interval are stored. It should be noted that other parameters measured by the IMD 10 can also be summarized using the above techniques, for example, for parameters such as heart rate, activity level, and temperature.

As described above, in certain embodiments, the IMD 10 can provide summary forms of data for one or more of the parameters monitored by the IMD 10. In certain embodiments, one of these monitored parameters includes heart rate. As such, as described above, one or more heart rate values can be selected to be representative for storage intervals of a certain designated length. In certain embodiments, the designated length of the storage intervals is five minutes; however, the invention should not be limited to such. As should be appreciated, the storage interval length is generally variable; however, certain trade-offs need to be taken into account prior to its designation. For example, if the storage interval length is set to be short in duration, the resolution of the data is increased; however, the storage rate of the data is also increased. As such, a better representation of the data as a whole can be provided, but the rate at which the memory of the IMD 10 fills up is increased, requiring transfer of the data from the IMD 10 to occur more frequently. Conversely, if the storage interval length is set to be long in duration, the resolution of the data is decreased; however, the storage rate of the data is decreased. As such, the rate at which the memory of the IMD 10 fills up is decreased, prompting downloads of the data from the IMD 10 to occur less frequently, but the representation of the data as a whole is generally compromised. In turn, the data representation may lead to misidentification of arrhythmic events. In turn, as should be appreciated, the setting of the storage interval length requires careful consideration.

Figure 2:
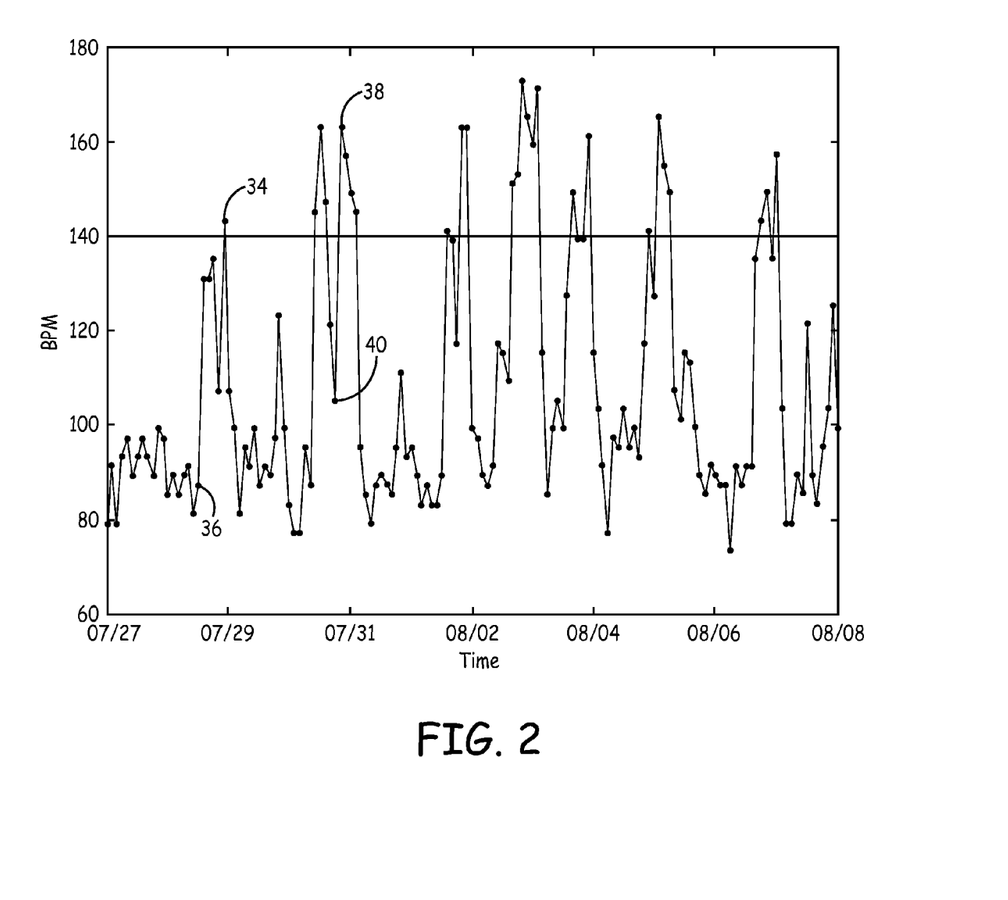
FIG. 2 is an exemplary plot of a trend line for upper percentile heart rate values over a time period in accordance with certain embodiments of the invention.

In certain embodiments, the one or more heart rate values selected for storage by the IMD 10 includes at least an upper percentile value (e.g., a $94^{th}$ percentile value). An exemplary plot of a trend line for the upper percentile values for a patient (each corresponding to a storage interval length) over a certain period of time is illustrated in FIG. 2. As shown, the trend line of the upper percentile values includes heart rates ranging from about eighty beats per minute to about one-hundred seventy-five beats per minute. As also exemplified, the trend line for the upper percentile values is shown over a thirteen-day duration (e.g., as shown, beginning on July 27 and ending on August 8). In addition, as shown, there are approximately twenty-four values recorded for every two days of operation of the IMD. As such, for this example, the storage interval length set for the IMD is generally about two hours. However, as should be appreciated from the above discussion, this storage interval length may be considered too long, resulting in too much of a decreased resolution of the data for adequate analysis purposes. As such, it should be appreciated that the plot of FIG. 2 is simply provided for illustrative purposes, and the invention should not be limited to such.

As described herein, embodiments of the invention involve using modes of statistical analysis to identify and/or assess arrhythmic events (e.g., atrial fibrillation). For example, with respect to single chamber IMDs, a lead of the IMD can be typically inserted in one of the heart chambers (e.g., the right ventricle). As such, the modes of analysis can be used to identify and/or assess arrhythmias occurring in the ventricles and/or the atria of the heart via data collected from such single lead. With respect to multi-chamber IMDs, multiple leads of the IMDs are typically inserted respectively in one of the ventricles and the atria. While the multiple leads may generally provide enough data to identify and/or assess arrhythmias occurring in the ventricles and/or atria of the heart, the modes of analysis can be used as a confirmatory mechanism. In turn, such modes of statistical analysis can aid a medical professional in evaluating patient data to diagnose the patient.

In certain embodiments, the modes of statistical analysis can be provided outside the IMD 10, e.g., by a programmer, monitor, or other processing device located remote from the IMD 10. As such, the modes of statistical analysis can be performed without involving further processing and/or additional circuitry for the IMD 10. However, the invention should not be limited to such. It should be appreciated that such modes of statistical analysis can just as well be performed by the IMD 10 and still be within the spirit of the invention.

In certain embodiments, one such mode of statistical analysis is referenced herein as the "criteria mode". The "criteria mode" involves determining whether the data meets certain criteria so as to signal the presence of an arrhythmic event. In certain embodiments, a first criterion involves determining whether a value exceeds a certain set heart rate threshold. As should be appreciated, during an arrhythmic event, the heart rate is generally well above the normal heart rate of a patient. Since patients have differing normal heart rates, the threshold is carefully selected so as to correspond to the patient's normal heart rate, and can be altered from time to time by the medical professional over the patient's life. For example, one patient's normal heart rate may be seventy beats per minute. As such, the heart rate threshold selected for such patient may be two times their normal heart rate, or one-hundred forty beats per minute. In turn, when using the "criteria mode", a determination is made with respect to the upper percentile value determined for each storage interval as to whether the corresponding value exceeds this heart rate threshold. With reference to FIG. 2, going from left to right on the x-axis with respect to the upper percentile values plotted, it is illustrated that the first value that exceeds this selected threshold occurs roughly on July 29. As such, this value, referenced as 34, satisfies the first criteria.

In turn, the "criteria mode" determines whether a second criterion is met so as to indicate an arrhythmic event. As should be appreciated, the onset of an arrhythmic event is often represented by a dramatic increase of the patient's heart rate from normal. As such, in certain embodiments, the "critical mode" determines whether the heart rate difference between value 34 and values occurring prior to value 34 exceed a certain designated amount. Again, as described above, each patient is different with respect to his or her cardiac condition. As such, the designated difference amount may be selected higher for some patients than for others. Again, it should be appreciated that such difference amount needs to be carefully selected based on the patient's condition, and can be altered from time to time by the medical professional over the patient's life. In one example, the difference amount may be selected by the medical professional to be forty beats per minute.

As such, in certain embodiments, the "criteria mode" examines one or more values prior to the value 34 to determine whether the difference in heart rate between the value 34 and any one of the prior values exceeds the set difference amount. As can be appreciated, one would have to go back five values prior to value 34 to show a value 36 that meets this second criteria. However, as described above, since the storage intervals shown by the plot of FIG. 2 generally represent two hour durations, it is safe to say that the ten hour duration between values 36 and 34 signals are probably not related by an arrhythmic event. As such, one must also carefully select the quantity of values the statistical analysis is to consider prior to a value meeting the first criteria in order to adequately determine whether an arrhythmic event has occurred. In the case of the plot of FIG. 2, one is likely to only go back one value and see if the difference between a first value meeting the first criteria and the difference between the first value and the value occurring just prior to the first value meets the second criteria. Such a case is shown by value 38 occurring roughly on July 31. As shown, the value 38 is above the set heart rate threshold of one-hundred forty beats per minute (meeting the first criteria) and the difference between the value 38 and a value 40 occurring just prior to the value 38 exceeds the forty beats per minute difference amount (meeting the second criteria). As such, by the "criteria mode" of statistical analysis, the value 38 would indicate conditions for an arrhythmic event.

As shown by the above-described statistical analysis, the trade-off concerning storage interval length has an obvious effect on the determination of whether the second criteria is met. In turn, the number of values the "criteria mode" checks in determining whether the second criteria is met should be decided with consideration being made to the length of the storage interval length. The above example indicates a scenario in which the number of values needs to be limited due to the occurrence of potential false positives for the statistical analysis. However, in certain embodiments, when the storage interval length is selected to be five minutes (as described above), the number of values that can then be considered in the second criteria analysis can be expanded from just the prior value. In such certain embodiments, the number of prior values considered can be three prior values; however, as should be appreciated, the invention should not be limited to such. In addition, in order to filter out other false positives for the statistical analysis, an activity sensor would generally be used to filter out data that is brought on by physical activity by the patient 12. As should be appreciated, such activity sensors can be used to characterize and mark and/or filter out data that is the result of such physical activity by the patient 12. As such, the marked or filtered data is eliminated prior to or alternatively during the statistical analysis of the data.

Figure 3:
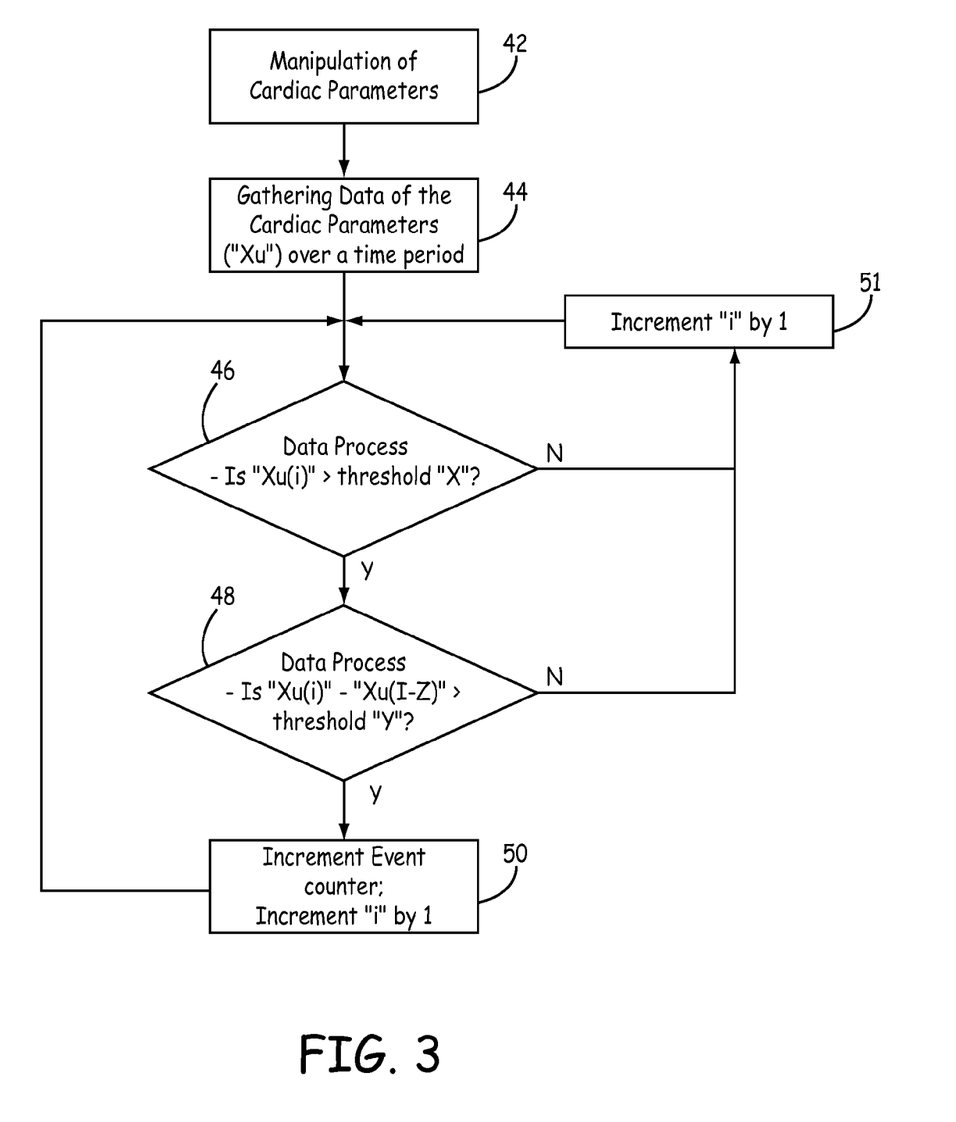
FIG. 3 is a flow chart illustrating a method of identifying and/or assessing arrhythmic events from data as exemplified in FIG. 2.

FIG. 3 shows a flowchart for the above "criteria mode" of statistical analysis. As shown, a first step 42 involves a manipulation of one or more cardiac parameters (by the summarizing function of the IMD 10 described above) and storage of the values within the IMD 10. A next step 44 involves a gathering of certain data "Xu" of the one or more cardiac parameters stored within the IMD 10. As mentioned above, this gathering can be represented by the IMD 10 gathering such data "Xu" from the memory of the IMD 10 for analysis by the IMD 10, or conversely, by the IMD 10 transferring such data "Xu" from the memory of the IMD 10 to a programmer, monitor, or other processing device for subsequent analysis. As illustrated above in FIG. 2, in certain embodiments, the data "Xu" gathered can involve upper percentile heart rate values (e.g., $94^{th}$ percentile values) for a specific time period (involving a plurality of consecutive storage intervals, wherein each storage interval is denoted an increment of "i"). However, the invention should not be limited to such. For example, in other embodiments, the data "Xu" can involve averaged heart rate values (e.g., upper percentile values), where each averaged heart rate value is derived from heart rate measures from a plurality of consecutive storage intervals over the specific period of time (with each plurality of consecutive storage intervals being denoted an increment of "i"). A further step 46 involves going through the data "Xu" sequentially (e.g., over the "i" storage intervals) to determine if and when the first criteria of the above statistical analysis is met (with "i" being set to one). As described above, the first criteria involves determining if the corresponding data "Xu" exceeds a set heart rate threshold "X". As exemplified with respect to FIG. 2, in certain embodiments, such heart rate threshold "X" may be set as one-hundred forty beats per minute.

If a value "Xu(i)" within the data "Xu" exceeds a set heart rate threshold "X", thereby meeting the first criteria, a next step 48 involves determining whether the difference between the value "Xu(i)" and any of "Xu(i–Z)" values of the data "Xu" occurring prior to the value "Xu(i)" exceed a set threshold amount "Y". As exemplified with respect to FIG. 2, "Z", which corresponds to the quantity of prior data values checked, may be set to one, and "Y" may be set to forty beats per minute; however, as described above, the invention should not be limited to such. If any of the differences between the value "Xu(i)" and the "Xu(i–Z)" values of the data "Xu" exceed the set threshold amount "Y", a next step 50 involves the "criteria mode" determining that conditions have been met for an arrhythmic event. As such, during step 50, a counter is triggered, so as to keep track of the number of such events occurring during analysis of the data "Xu". In addition, a further counter is triggered to increment "i" by one for subsequent evaluation of the next value "Xu(i+1)" of the data "Xu". Subsequently, the analysis is looped back between steps 44 and 46 for analysis involving the next data value "Xu(i+1). As should be appreciated, if the criteria is not met in either of the steps 46 or 48 (respectively corresponding to the steps involving the first and second criteria), the further counter is triggered to increment "i" by one in step 51 for subsequent evaluation of the next value "Xu(i+1)" of the data "Xu". Subsequently, the analysis is looped back between steps 44 and 46 for analysis involving the next data value "Xu(i+1)".

Using the same summarizing principles as described above for one or more of the cardiac parameters stored by the IMD 10, further modes of statistical analysis can be used to identify and/or assess arrhythmic events (e.g., atrial fibrillation). One further mode of statistical analysis is the "ratio mode". In certain embodiments, for selected storage interval lengths, an upper percentile value (e.g., a $94^{th}$ percentile value), a median value, and a lower percentile value (e.g., a $6^{th}$ percentile value) are determined for the one or more cardiac parameters and stored within the IMD 10 for each storage interval. In certain embodiments, one cardiac parameter involves heart rate. As graphically illustrated in FIG. 4, the heart rate values can be plotted to show trend lines for each value over a designated period of time. As exemplified in FIG. 4, the trend lines for each value are shown over a seven-day duration (e.g., as shown, beginning on June 26 and ending on July 2). As should be expected, the trend line 52 for the upper percentile values is the highest curve on the plot, the trend line 54 for the median values is the next highest curve on the plot, and the trend line 56 for the lower percentile values is the lowest curve on the plot.

Figure 4:
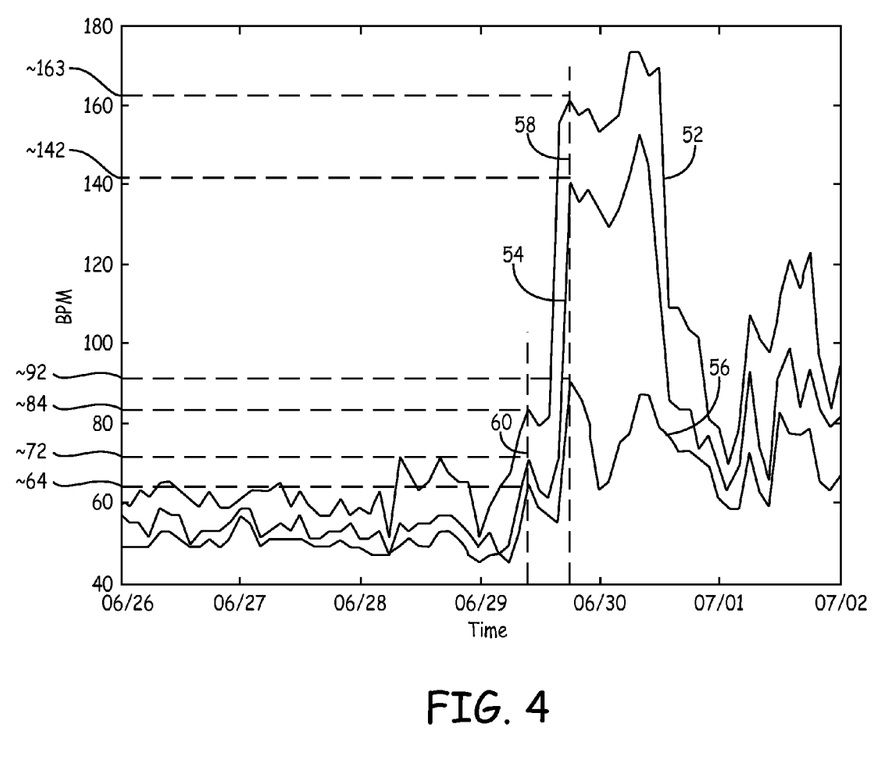
FIG. 4 is an exemplary plot of trend lines for upper percentile, median, and lower percentile heart rate values over a time period in accordance with certain embodiments of the invention.

As shown, the three trend lines 52, 54, and 56 are continuously in flux as to their relative distances with each other. In turn, the distribution of the corresponding heart rate values collected during the designated period of time of the plot is illustrated. For example, as the median trend line 54 approaches the upper percentile trend line 52, the majority of values are located closer to the upper percentile. In certain embodiments, the "ratio mode" involves a determination of the distribution skewness of the heart rate values. In turn, for each storage interval, the "ratio mode" involves determining a distance between the upper percentile value and the median value and determining a distance between the median value trend line and the lower percentile value. By subsequently computing a ratio of these distances for the corresponding storage interval, the "ratio mode" can be used to identify the presence of an arrhythmic event. By further tracking the ratios for a number of consecutive storage intervals, the "ratio mode" can be used to provide an estimation as to the duration of the arrhythmic event.

As should be appreciated, a plurality of different ratios can be determined by making comparisons of different results. For example, in certain embodiments, for each storage interval, the difference between the upper percentile value and the median value can be compared to the difference between the median value and the lower percentile value; however, the invention should not be limited as such. During an arrhythmia, it should be appreciated that the median trend line 54 generally rises closer to the upper percentile trend line 52 and moves away from the lower percentile trend line 56. This is because the heart rate of a patient is generally elevated fairly consistently over such an event. As such, in calculating the ratio using the above-described exemplary calculation (when dividing the distance between the upper percentile value and the median value by the distance between the median value and the lower percentile value), the result tends to be a value less than unity.

For example, with reference to FIG. 4, for the storage interval corresponding to the first spike in the plateau of the upper percentile (referenced by line 58), the upper percentile value is about one-hundred sixty-three beats per minute, the median value is about one-hundred forty-two beats per minute, and the lower percentile value is about ninety-two beats per minute. As such, in using the difference and ratio calculation exemplified above, a ratio of 0.42 is calculated. In comparison, with further reference to FIG. 4, for the storage interval length corresponding to the previous spike of the upper percentile trend line (referenced by line 60), the upper percentile value is about eighty-four beats per minute, the median value is about seventy-two beats per minute, and the lower percentile value is about sixty-four beats per minute. In turn, the same comparison of these differences results in a ratio of 1.50. In certain embodiments, for many patients, it has been found that the ratio calculated in normal conditions for the heart tends to be about 1.00. As such, the statistical analysis can be used to indicate conditions representing an arrhythmia (e.g., when the ratio starts to approach zero) and/or the general duration of the arrhythmia. For instance, a low ratio indicates that the arrhythmia lasted a higher percentage of the storage interval, indicating a higher burden. In addition, a low ratio over multiple consecutive intervals indicates a long-lasting arrhythmia. As discussed herein, information from an activity sensor or other type of sensor may be used to help confirm that the low ratio represents an arrhythmia and not just a high rate due to physical exertion.

It should be appreciated that over time, certain ratios or ranges of ratios may be found to be linked to specific arrhythmias. As such, it should be appreciated that the above statistical analysis can be used not only to identify conditions representing arrhythmias and/or the general duration of arrhythmias, but also in identifying the specific arrhythmia that affected the patient based on its ratio or range of ratios during such event. In addition, while the above embodiment describes one calculation for determining the ratio based on a certain comparison of the distances, it should be appreciated that other calculations can be used alternatively. It should be appreciated that while using different calculations may result in different ratios, such would still be within the spirit of the invention when used to offer information related to the detection and/or assessment of arrhythmic events.

With further reference to FIG. 4, the "ratio mode" of statistical analysis can be enhanced to further aid medical professionals in providing diagnoses for the patient. In certain embodiments, the "ratio mode" can be used to calculate a distance between values on the upper and lower percentile trend lines 52, 56 for one or more storage interval lengths. As should be appreciated, such a distance (either alone or when compared with the distances between the upper percentile value and median value and/or the distance between the median value and the lower percentile value), when taken over the length of the time period of the trend lines 52, 56, would enable the "ratio mode" to provide information as to the variability of the patient's heart rate. This variability information, when combined with the calculated ratio information, can further provide a medical professional insight as to the condition of the patient's heart.

In certain embodiments, the "ratio mode" can also be further enhanced by continuously averaging the deviation of the calculated ratios from a fixed or dynamic base line ratio (e.g., a long-term average or a fixed threshold) to detect sudden shifts in the relationship between the trend lines 52, 54, and 56. In certain embodiments, this continuous averaging can be provided via a cumulative sum. In turn, any deviation between these two ratios is averaged over a certain historical period of time and such averaged deviation is cumulatively added to deviations similarly calculated for prior storage intervals. As such, when the calculated ratio deviates from the base line ratio for any extended period of time (e.g., exhibiting high rate burden), the cumulative sum is found to show a significant output. The output of the cumulative sum is generally found to be proportional to the magnitude of high rate burden, or length of the event. As such, using the output of the cumulative sum as a basis, the high rate burden can, in turn, be plotted. Such a graphical representation is shown in FIG. 5, with the high rate burden being plotted across the same time period that is used for the trend lines 52, 54, and 56 of FIG. 4.

Figure 5:
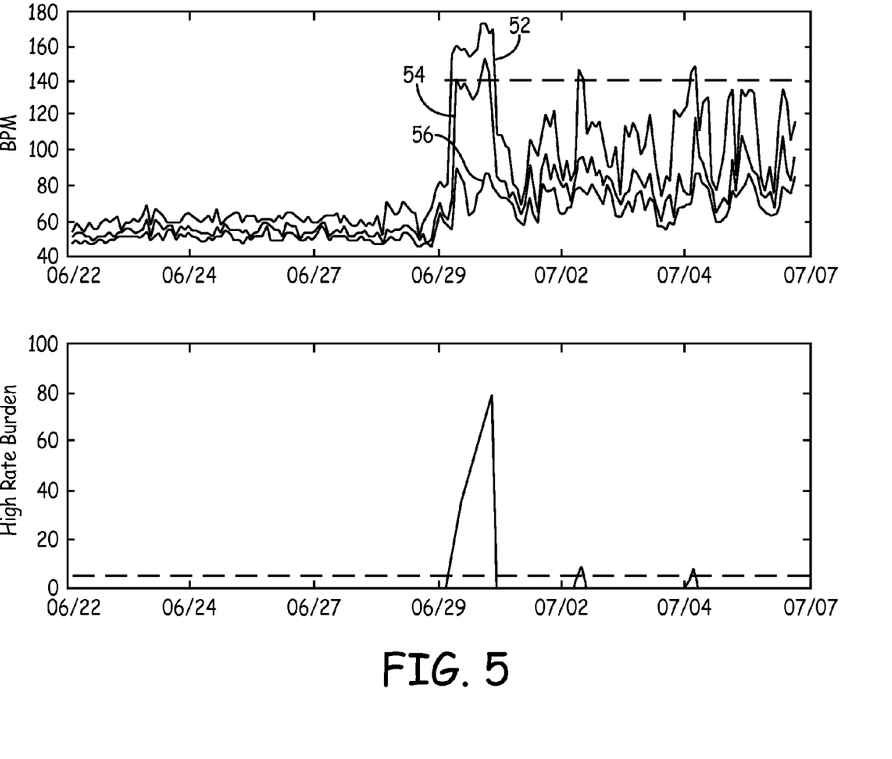
FIG. 5 is a series of plots including the plot of FIG. 4 and an exemplary plot of high rate burden over the time period of the plot of FIG. 4 in accordance with certain embodiments of the invention.

As illustrated, the upper plot of FIG. 5 is the same as shown in FIG. 4; however, the lower plot represents the high rate burden exhibited for the trend lines 52, 54, and 56 of the upper plot based on the output of the cumulative sum. As illustrated, the high rate burden is detected in the regions of FIG. 4 in which the median trend line 54 is closest to the upper percentile trend line 52 and furthest from the lower percentile trend line 56. As described with respect to the "ratio mode", based solely on the ratio calculations, such regions are generally indicative of conditions representing an arrhythmia because the calculated ratio for such storage intervals tend to approach zero (e.g., below 0.5). However, using the lower plot of FIG. 5, one can see high rate burden is similarly detected during such regions via the output of the cumulative sum. In turn, the lower plot provides further evidence for the "ratio mode" of conditions representing an arrhythmia. In addition, by the magnitude of the high rate burden illustrated in the lower plot, the enhanced "ratio mode" can be used to further indicate the length in time of the arrhythmic event. For example, for high rate burden values that are found to exceed a selected threshold, the "ratio mode" would indicate the presence of an arrhythmia.

Figure 6:
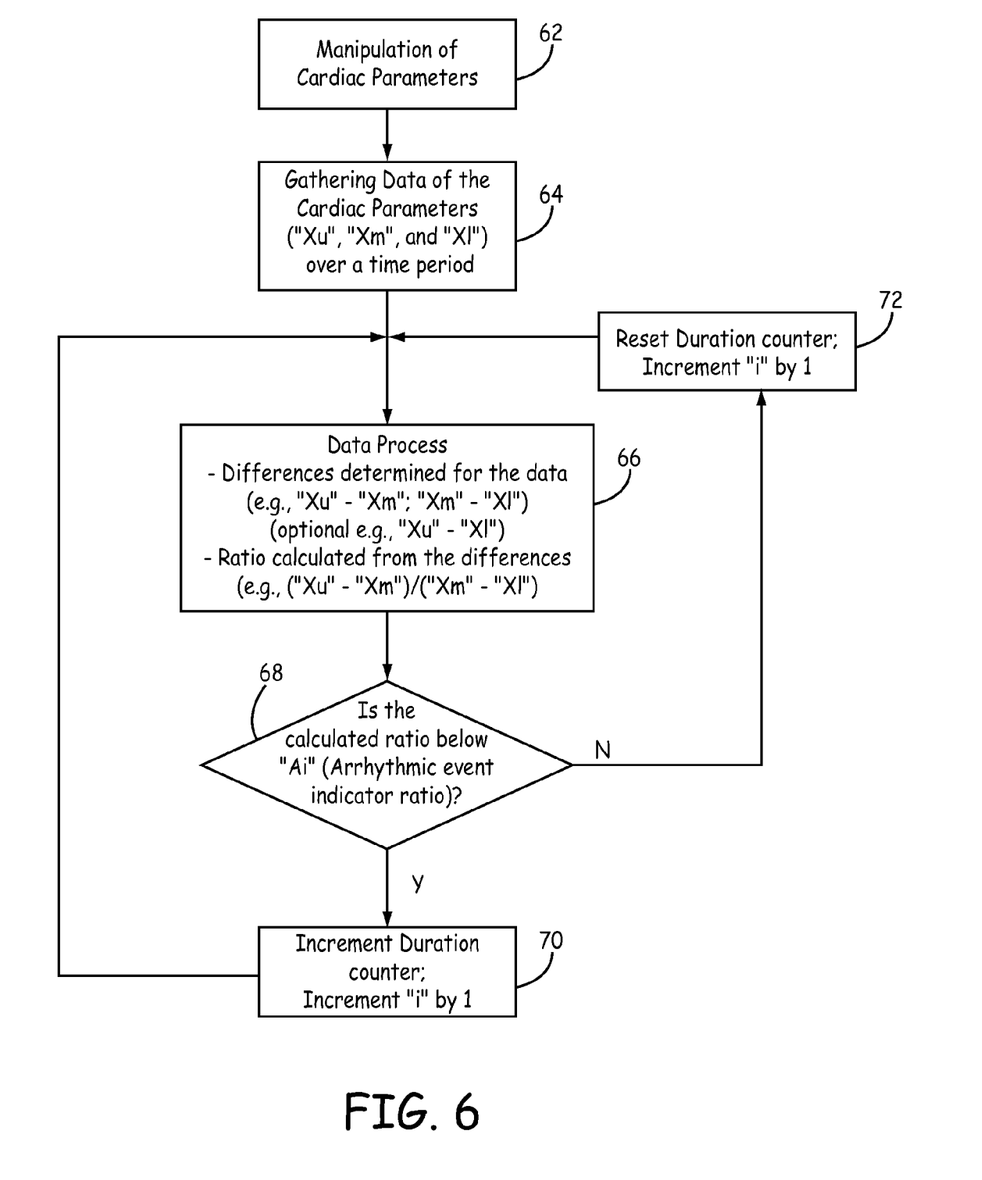
FIG. 6 is a flow chart illustrating a method of identifying and/or assessing arrhythmic events from data as exemplified in FIG. 4.

FIG. 6 shows a flowchart for one embodiment of the above "ratio mode" of statistical analysis. As shown, a first step 62 involves a manipulation of one or more cardiac parameters (by the summarizing function of the IMD 10 described herein) and storage of the values within the IMD 10. A next step 64 involves a gathering of certain data (e.g., "Xu", "Xm", and "Xl") of the one or more cardiac parameters stored within the IMD 10. As mentioned above, this gathering can be represented by the IMD 10 gathering such data from the memory of the IMD 10 for analysis by the IMD 10, or conversely, by the IMD 10 transferring such data from the memory of the IMD 10 to a programmer, monitor, or other processing device for subsequent analysis. As illustrated above in FIG. 4, in certain embodiments, the data "Xu", "Xm", and "Xl" gathered involves upper percentile heart rate values (e.g., $94^{th}$ percentile values), median heart rate values, and lower percentile values (e.g., $6^{th}$ percentile values) for a specific time period (involving a plurality, denoted by "i", of consecutive storage interval lengths).

A further step 66 involves going through the data "Xu", "Xm", and "Xl" sequentially (over the "i" storage intervals) to determine differences of the values. In turn, a ratio is determined for the corresponding storage interval. As described above, one ratio calculation that can be used is based on a comparison of the difference between the upper percentile value and the median value and the difference between the median value and the lower percentile value.

Based on the value of the ratio, a next step 68 involves the "ratio mode" determining whether or not the calculated ratio is below Ar (an arrhythmic event indicator ratio threshold). In certain embodiments, such ratio can be generally about 0.5; however the invention should not be limited to such. As described above, generally when the ratio is found to approach zero (so as to be below Ar), such ratio can be indicative of an arrhythmic event. As such, during step 70, a counter is triggered, so as to keep track of the duration of such arrhythmic event occurring during analysis of the data "Xu", "Xm", and "Xl". In addition, a further counter is triggered to increment "i" by one for subsequent evaluation of the next value "Xu(i+1)" of the data "Xu", "Xm(i+1)" of the data "Xm", and "Xl(i+1)" of the data "Xl". Subsequently, the analysis is looped from step 70 back between steps 64 and 66 for analysis involving the next data values "Xu(i+1)", "Xm(i+1)", and "Xl(i+1)". As should be appreciated, if the calculated ratio is determined as not being below AR in the step 68, the duration counter is reset and the further counter is triggered to increment "i" by one in step 72 for subsequent evaluation of the next values "Xu(i+1)", "Xm(i+1)", and "Xl(i+1)" of the data. Subsequently, the analysis is looped from step 68 to step 72 and subsequently back between steps 64 and 66 for analysis involving the next data values.

In certain embodiments, as shown in step 66, the distance between the upper percentile value "Xu(i)" and the lower percentile value "Xl(i)" can also be calculated in combination with the other differences mentioned above. As described above, such a distance value (either alone or when compared with the distances between the upper percentile value and median value and/or the distance between the median value and the lower percentile value) would enable the statistical analysis to provide information as to the variability of the patient's heart rate.

Figure 7:
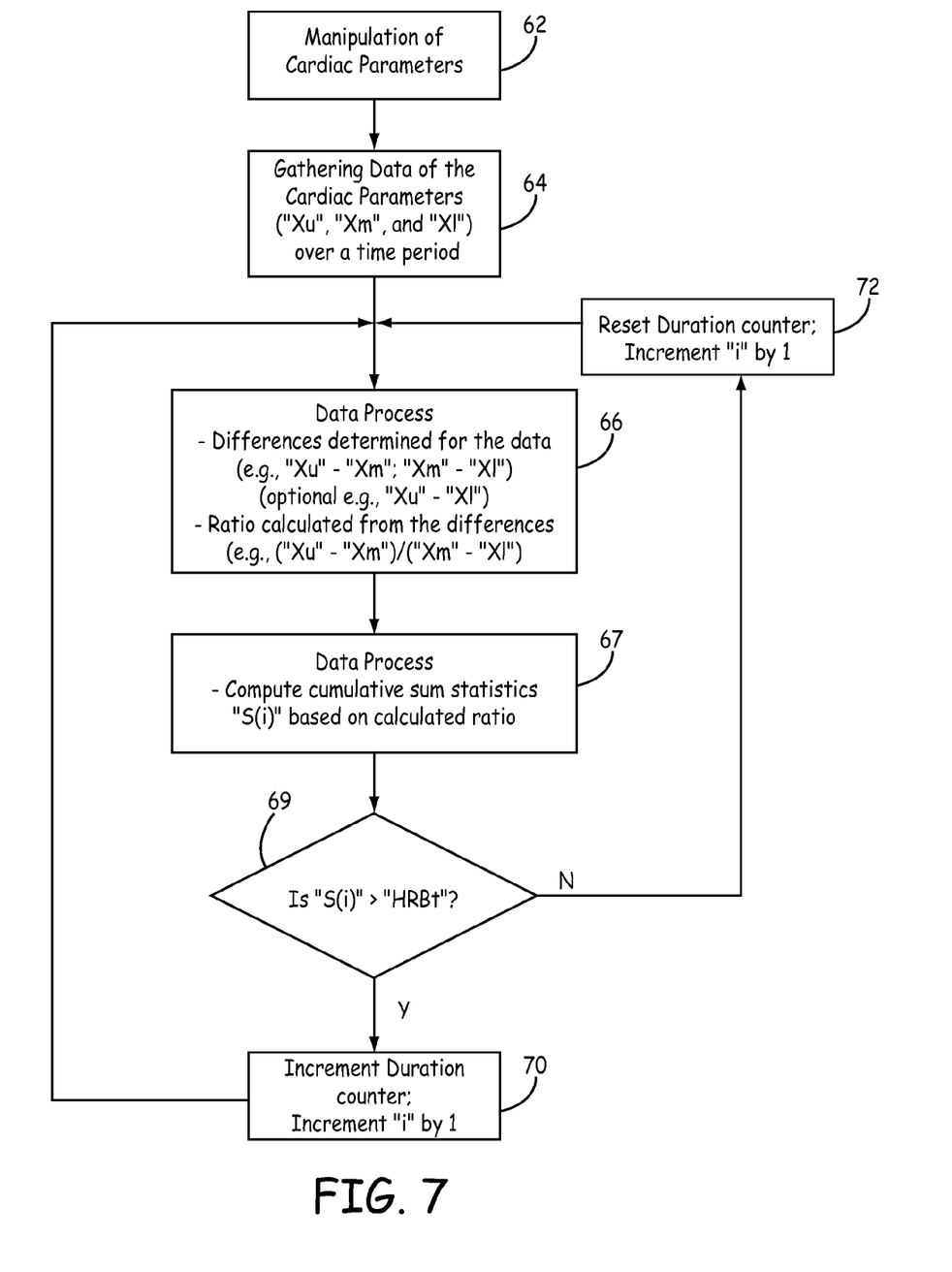
FIG. 7 is a flow chart illustrating a method of identifying and/or assessing arrhythmic events from data as exemplified in FIG. 5.

FIG. 7 shows a flowchart similar to the flowchart of FIG. 6 with steps 62-66, 70, and 72 being the same. Step 67 involves comparing the ratio calculated in step 66 with a dynamic base line ratio (e.g., a long-term average or a fixed threshold) for the patient. The deviation between these ratios is subsequently averaged over a certain historical period of time and such averaged deviation is cumulatively added to deviations similarly calculated for previous storage intervals. As described above, in certain embodiments, this aggregate functionality is enabled via the use of a cumulative sum. As further described above, when the calculated ratio deviates from the base line ratio for any extended period of time (e.g., exhibiting high rate burden), it is found that the output of the cumulative sum begins to show a significant output. For example, the output of the cumulative sum "S(i)" can be computed with the following equation:

a. "$S(i)$"="$S(i-1)$"+$y(i)-k$, i. where k=a limiting constant, and $y(i)=C[x(i)-\mu(i)]$, where C=an averaging or normalization constant,
x(i)=the calculated ratio, and
μ(i)=the baseline ratio.

The output of such cumulative sum is found to be proportional to a magnitude of the high rate burden. As such, in step 69, the output of the cumulative sum "S(i)" is compared to a high rate burden threshold, HRBt. If the output exceeds the threshold, the "ratio mode" can further indicate the presence of an arrhythmia. As such, during step 70, the same counters described above with respect to FIG. 6 are triggered. Subsequently, the analysis is looped from step 70 back between steps 64 and 66 for further analysis. As should be appreciated, if the criteria is not met in the step 69, the duration counter is reset and the further counter is triggered to increment "i" by one in step 72 for subsequent evaluation of the next values "Xu(i+1)", "Xm(i+1)", and "Xl(i+1)" of the data. Subsequently, the analysis is looped back step 69 through step 72 and subsequently between steps 64 and 66 for analysis involving the next data values.

As described above, further modes of statistical analysis with respect to cardiac parameters can be used to aid the medical professional in identifying and/or assessing arrhythmic events (e.g., atrial fibrillation). One further mode of statistical analysis is the "variability mode". In certain embodiments, the cardiac parameters involve heart rate and pressure parameters of the heart. As graphically illustrated through a series of plots shown in FIG. 8, a number of heart parameters are individually plotted. The upper plot shows a trend line for a patient's heart rate over a two and a half minute time period (e.g., from 16:12:14 through 16:14:44). As indicated on the upper plot, the left half of the upper plot shows a high rate event, with heart rates ranging from about 150 beats per minute to about 155 beats per minute. Upon triggering of therapy (e.g., by a corresponding IMD) at about 16:13:29, the heart rate is shown to steadily decrease.

Figure 8:
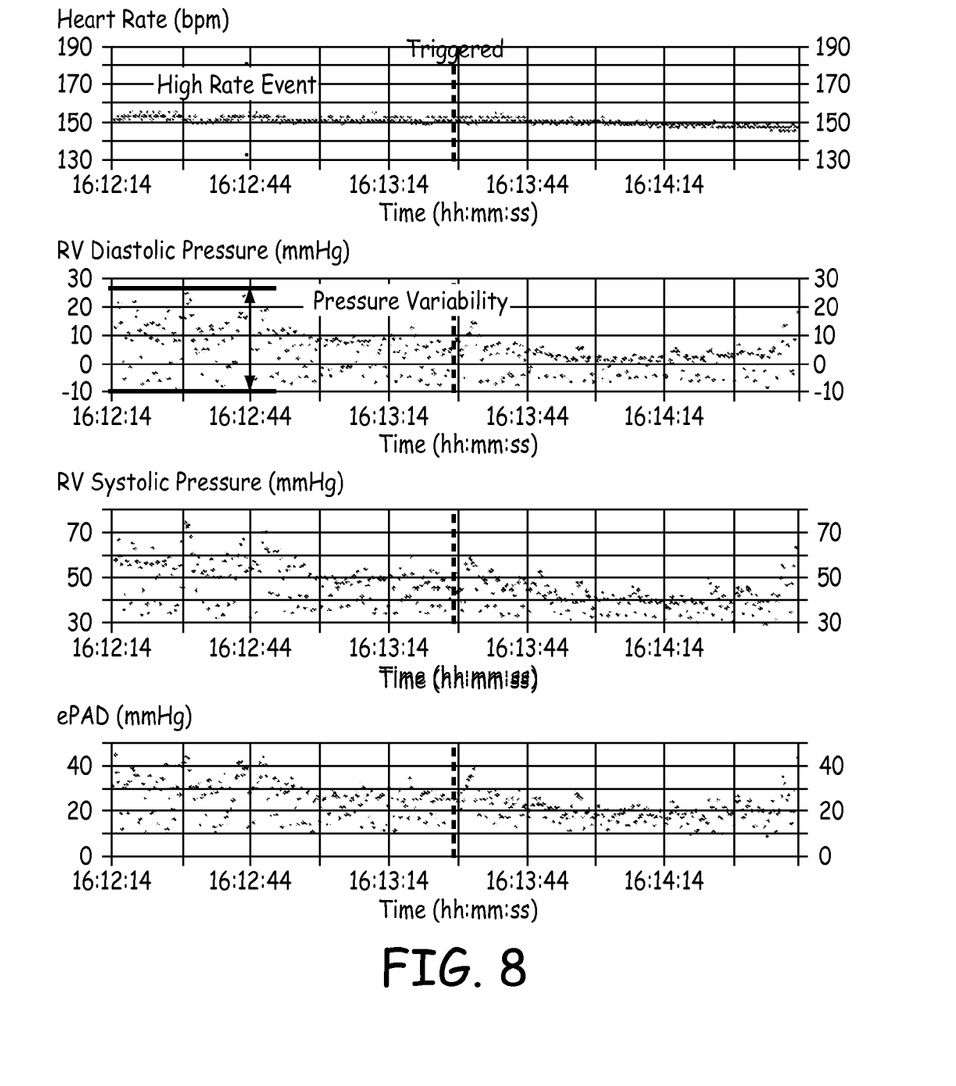
FIG. 8 is a exemplary series of plots of heart rate and pressure parameters over a time period in accordance with certain embodiments of the invention.

With reference to the three lower plots, pressure parameters such as RV diastolic pressure, RV systolic pressure, and ePAD are plotted over the same time period as described above with respect to the upper plot. As can be appreciated, in comparing the heart rate plot to the pressure parameter plots, it is generally shown that the variability of the heart pressure parameters increase significantly during high rate events. In turn, computation of such pressure variability can be used as a confirmatory mechanism for the presence of high rate events (e.g., atrial arrhythmias). In certain embodiments, as illustrated in the RV diastolic plot, the "variability mode" can determine the variability by calculating a distance between upper and lower values of a certain time period of one or more of the pressure parameters. As described above with respect to FIG. 5, by continuously averaging the deviation of these calculated distances from a dynamic base line distance for the patient, the "variability mode" can be used as a confirming factor in identifying the presence of arrhythmias. In certain embodiments, this continuous averaging can be provided with the use of a cumulative sum. In turn, any deviation between these two distances is averaged over a certain historical period of time and such averaged deviation is cumulatively added to deviations similarly calculated for prior storage intervals. As such, when the calculated distance deviates from the base line distance for any extended period of time, the cumulative sum is found to show a significant output. Upon comparing this output to a set threshold level, the "variability mode" would provide an indicator of the presence of an arrhythmia. It should be appreciated that the "variability mode" would simply provide such an indicator, and would generally need to be supported by one or more further criteria in order to be determinative.

Figure 9:
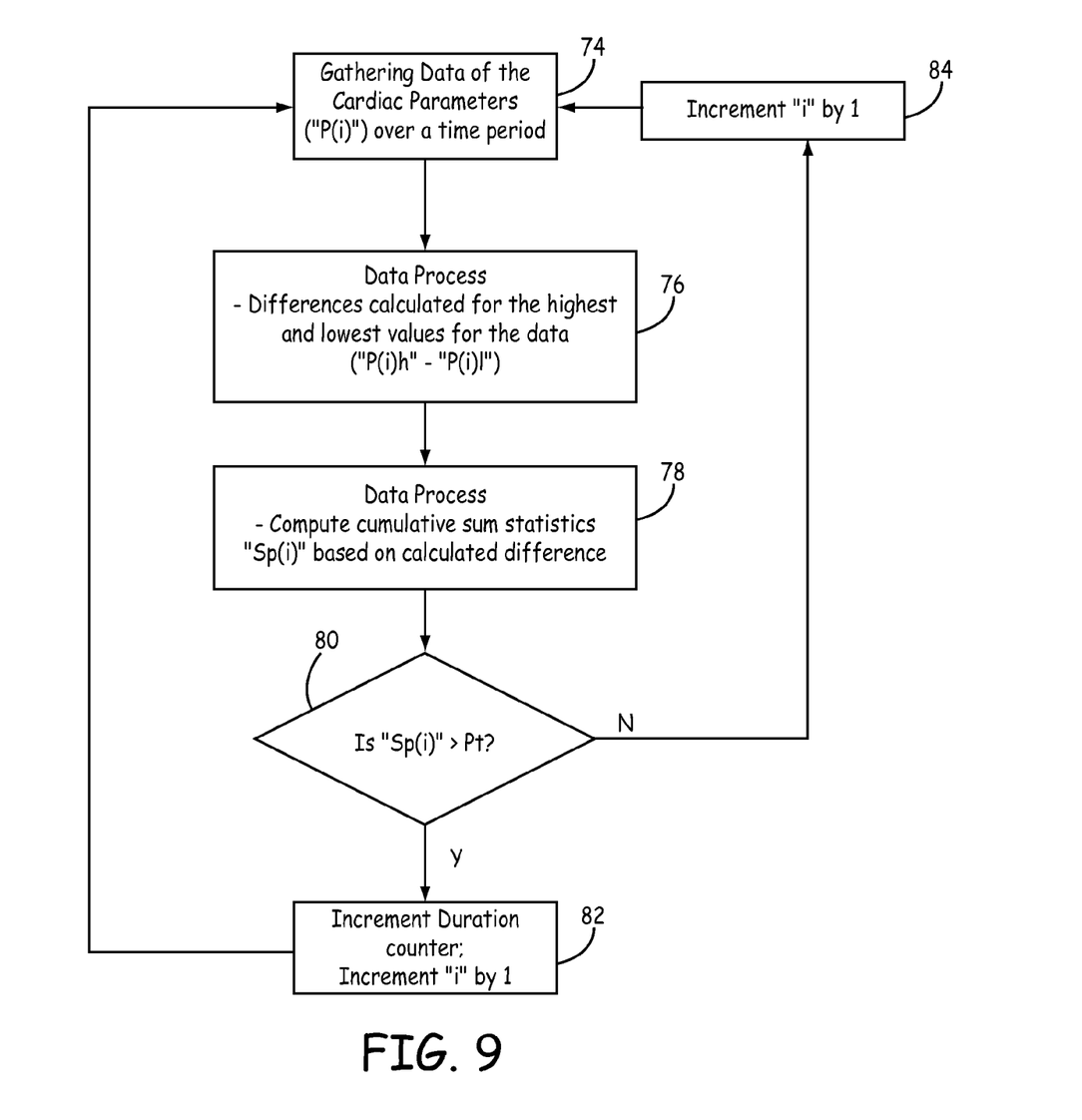
FIG. 9 is a flow chart illustrating a method of providing an indicator to identifying and/or assessing arrhythmic events from data as exemplified in FIG. 8.

FIG. 9 shows a flowchart for one embodiment of the above "variability mode" of statistical analysis. As shown, a first step 74 involves a gathering of certain data (e.g., "P(i)") of the one or more cardiac parameters stored within the IMD 10. As mentioned above, this gathering can be represented by the IMD 10 gathering such data from the memory of the IMD 10 for analysis by the IMD 10, or conversely, by the IMD 10 transferring such data from the memory of the IMD 10 to a programmer, monitor, or other processing device for subsequent analysis. As illustrated above in FIG. 8, in certain embodiments, the data "P(i)" gathered involves a pressure parameter for a specific time period "i" ("i" equaling one initially). A further step 76 involves going through the data "P(i)" sequentially to determine the highest value "P(i)h" and lowest value "P(i)l" of the "P(i)" data. In turn, the difference is calculated between such highest and lowest values. Step 78 involves comparing the difference calculated in step 76 with a dynamic base line distance (e.g., a long-term average or a fixed threshold) for the patient. The deviation between these ratios is subsequently averaged over a certain period of time and such averaged deviation is cumulatively added to deviations similarly calculated for previous storage intervals. As described above, in certain embodiments, this aggregate functionality is enabled via the use of a cumulative sum. As further described above, when the calculated ratio deviates from the base line distance for any extended period of time (e.g., exhibiting high rate burden), it is found that the output of the cumulative sum shows a significant output. The output of the cumulative sum "Sp(i)" is found to be proportional to a magnitude of the high rate burden. As such, in step 80, the output of the cumulative sum "Sp(i)" is compared to a designated threshold "Pt". If the magnitude exceeds the threshold, the "variability mode" can further provide an indicator as to the presence of an arrhythmia. As such, during step 82, a counter is triggered, so as to keep track of such indicators during analysis of the data "P(i)". In addition, a further counter is triggered to increment "i" by one for subsequent evaluation of the next set of data "P(i+1)" Subsequently, the analysis is looped back to step 74 for further gathering of data "P(i+1)". As should be appreciated, if the criteria is not met in step 80, the further counter is triggered to increment "i" by one in step 84 for subsequent evaluation of the next set of data "P(i+1)". Subsequently, the analysis is looped back to step 74 for analysis involving the next data value "P(i+1)".

It should be appreciated that the exemplified pressure parameters gathered above with respect to the above "variability mode" of statistical analysis can be provided from a number of sources and should not be solely limited to IMDs to be within the spirit of the invention. In addition, in certain embodiments, based on the results of the statistical analyses provided by the above-described modes of analysis, the device providing the modes can provide instruction (e.g., telemetrically) to IMDs (e.g., implantable drug pumps) instead of requiring initial analysis by a medical professional. For example, in the case of a drug pump, based on the indication and/or duration of an arrhythmic event, the device utilizing the above modes of analysis may be able to instruct the drug pump to modify the amount of drugs provided to the patient. In addition, in certain embodiments, the specific type of arrhythmia may also be ascertained via the use of the modes. In turn, in certain embodiments, decisions normally provided by a medical professional with respect to certain diagnoses for the patient (e.g., regarding levels of medication needed) may instead be automatically provided in using the above modes. Further, it should be appreciated that one or more aspects of the modes of statistical analysis described herein can be combined to provide further modes of statistical analysis.

It will be appreciated the embodiments of the present invention can take many forms. The true essence and spirit of these embodiments of the invention are defined in the appended claims, and it is not intended the embodiment of the invention presented herein should limit the scope thereof.

The invention claimed is:

1. A non-transitory computer-readable medium programmed with instructions for performing a method of identifying and/or assessing patient arrhythmias, the medium comprising instructions for causing a programmable processor to:
    obtain sets of high, median, and low percentile measures of a heart parameter of a patient collected over a plurality of successive time intervals, each set of high, median, and low percentile measures corresponding to a respective time interval of the plurality of successive time intervals, the sets gathered from a memory of a medical device implanted within the patient;
    for each set, calculate a ratio corresponding to the magnitude of the gaps between the percentile measures; and
    using each ratio, for the time interval associated with each ratio, determine at least one of an indication of an arrhythmia and at least a partial duration of the arrhythmia.

2. The computer readable medium of claim 1, wherein the indication of the arrhythmia for the time interval associated with each ratio involves a determination that such ratio is below a predetermined ratio threshold.

3. The computer readable medium of claim 2, further including instructions to
    increment a counter for any storage interval in which such ratio is below the predetermined ratio threshold, whereby the counter is used to indicate the number of storage intervals defining the corresponding arrhythmia; and
    reset the counter for any storage interval in which such ratio is above the predetermined ratio threshold.

4. The computer readable medium of claim 1, further including instructions to:
    aggregate each ratio with a dynamic base line ratio for the patient; determine whether the aggregate exceeds a high rate burden threshold; and provide an indication of the presence of an arrhythmia for the time intervals associated with the ratios in which the aggregate exceeds the high rate burden threshold.

5. The computer readable medium of claim 4, further including instructions to
    increment a counter for any storage interval in which the aggregate exceeds the predetermined high rate burden threshold, whereby the counter is used to indicate the number of storage intervals defining the corresponding arrhythmia; and
    reset the counter for any storage interval in which the aggregate is equal to or below the predetermined high rate burden threshold.

6. The computer readable medium of claim 4, wherein the aggregating step involves the use of a cumulative sum.

* * * * *